United States Patent
Gunderson et al.

(10) Patent No.: US 7,167,747 B2
(45) Date of Patent: Jan. 23, 2007

(54) IDENTIFICATION OF OVERSENSING USING SINUS R-WAVE TEMPLATE

(75) Inventors: Bruce D. Gunderson, Plymouth, MN (US); Gillberg M. Jeffrey, Coon Rapids, MN (US); Jay M. Wilcox, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 532 days.

(21) Appl. No.: 10/436,626

(22) Filed: May 13, 2003

(65) Prior Publication Data

US 2004/0230233 A1 Nov. 18, 2004

(51) Int. Cl.
*A61N 1/372* (2006.01)
*A61N 1/39* (2006.01)

(52) U.S. Cl. ............... 607/9; 607/5; 607/27; 600/515; 600/518

(58) Field of Classification Search ............... 600/515, 600/518; 607/27–28
See application file for complete search history.

(56) References Cited

U.S. PATENT DOCUMENTS

| | | | | |
|---|---|---|---|---|
| 4,374,382 A | 2/1983 | Markowitz | ............. | 340/870.01 |
| 4,428,378 A | 1/1984 | Anderson et al. | ..... | 128/419 PG |
| 5,107,833 A | 4/1992 | Barsness | ............... | 128/419 PT |
| 5,117,824 A | 6/1992 | Keimel et al. | .......... | 128/419 D |
| 5,168,871 A | 12/1992 | Grevious | ............... | 128/419 PT |
| 5,193,550 A * | 3/1993 | Duffin | ......... | 600/510 |
| 5,292,343 A | 3/1994 | Blanchette et al. | ........... | 607/32 |
| 5,324,315 A | 6/1994 | Grevious | ..................... | 607/60 |
| 5,354,319 A | 10/1994 | Wyborny et al. | .............. | 607/32 |
| 5,383,909 A | 1/1995 | Keimel | ......................... | 607/7 |
| 5,447,519 A * | 9/1995 | Peterson | ........................ | 607/5 |
| 5,545,186 A | 8/1996 | Olson et al. | .................. | 607/14 |
| 5,558,098 A * | 9/1996 | Fain | ............................ | 600/519 |
| 5,620,466 A | 4/1997 | Haefner et al. | ................ | 607/5 |
| 5,755,736 A | 5/1998 | Gillberg et al. | ................ | 607/4 |
| 5,755,739 A | 5/1998 | Sun et al. | ..................... | 607/14 |
| 5,776,168 A | 7/1998 | Gunderson | ................... | 607/27 |
| 6,266,554 B1 * | 7/2001 | Hsu et al. | .................... | 600/515 |
| 6,393,316 B1 | 5/2002 | Gillberg et al. | ............. | 600/515 |

\* cited by examiner

*Primary Examiner*—George Manuel
*Assistant Examiner*—Nicole R. Kramer
(74) *Attorney, Agent, or Firm*—Michael C. Soldner; Girma Wolde-Michael

(57) ABSTRACT

A method and apparatus delivering therapy in an implantable medical device that includes sensing a first cardiac signal and detecting cardiac events via a first electrode configuration, determining the presence of an episode requiring therapy in response to the detected cardiac events, sensing a second cardiac signal via a second electrode configuration, comparing, in response to an episode being present, portions of the second cardiac signal corresponding to the detected cardiac events with a predetermined template, and determining whether to deliver therapy in response to the comparing.

6 Claims, 7 Drawing Sheets

IDENTIFICATION OF OVERSENSING USING SINUS R-WAVE TEMPLATE

TECHNICAL FIELD OF THE INVENTION

The present invention generally relates to implantable medical devices, and more particularly relates to reducing effects of oversensing in implantable medical devices.

BACKGROUND OF THE INVENTION

Implantable medical devices (IMDs) have many functions including the delivery of therapies to cardiac patients, neurostimulators, muscular stimulators, and others. Application of the present invention is described below in the context of implantable cardiac pacemakers and/or defibrillators, it being understood that the principles herein may have applicability to other implantable medical devices as well.

An example of an implantable medical device (IMD) includes a device commonly referred to as a pacemaker, which is used to stimulate the heart into a contraction if the sinus node of the heart is not properly timing, or pacing, the contractions of the heart. Modern implantable medical devices also perform many other functions beyond that of pacing. For example, a pacemaker/cardioverter/defibrillator (PCD) performs therapies such as defibrillation and cardioversion as well as providing several different pacing therapies, depending upon the needs of the user and the physiologic condition of the user's heart.

In typical use, a PCD is implanted in a convenient location usually under the skin of the user and in the vicinity of the one or more major arteries or veins. One or more electrical leads connected to the PCD are inserted into or on the heart of the user, usually through a convenient vein or artery. The ends of the leads are placed in contact with the walls or surface of one or more chambers of the heart, depending upon the particular therapies deemed appropriate for the user.

One or more of the leads is adapted to carry a current from the PCD to the heart tissue to stimulate the heart in one of several ways, again depending upon the particular therapy being delivered. The leads are simultaneously used for sensing the physiologic signals provided by the heart to determine when to deliver a therapeutic pulse to the heart, and the nature of the pulse, e.g., a pacing pulse or a defibrillation shock.

In the sensing mode, sense amplifiers coupled to the leads provide amplification to electrogram signals picked up by the sensing electrodes in the heart. The analysis of these signals by the PCD determines whether a therapy (a pacing pulse or a defibrillator shock) should be administered. If erroneous signals are detected by the PCD, an unnecessary therapy may be administered, providing an unnecessary pacing pulse or defibrillator shock to the patient. One cause of erroneous interpretation of sensing signals is oversensing, that is, the false detection of a depolarization event.

Sensing can be accomplished in a number of ways. If two bipolar leads are used, one lead is typically placed within the right ventricle of the heart and a second lead is placed within the right atrium of the heart. Both leads include two sensing elements: a tip electrode that is attached to the wall or surface of the heart, and a ring electrode that is located on the lead but removed some distance from the tip electrode. A high voltage coil located on one or both of the leads can also be used for sensing, as can the implanted PCD can itself. Some cardiac conditions require sensing at both the right ventricle and the right atrium, and still others may add sensing at the left ventricle via a third lead positioned within the coronary sinus. As a result, there are a large number of sensing paths and combinations available for use, depending upon the configuration and programming of the specific implantable device, and some PCDs can be configured to switch to an alternate sensing path if the primary path is determined to be faulty.

Oversensing of cardiac waves may be caused by lead fractures (e.g., conductor break, insulation break, adaptor failure), connectors (e.g. loose set screw), T-wave oversensing, R-wave oversensing, electromagnetic interference (EMI), and myopotentials. In the past, oversensing problems (e.g., myopotentials, T-wave oversensing) have been dealt with by modifying sense amplifiers, filters and PCD lead electrodes. In currently used PCDs the sense amplifiers have self adjusting sensing thresholds for sensitivity, so oversensing often occurs as a result of lead failure. Upon detection of an R-wave, the threshold of the sense amplifier is raised to about 75% of the R-wave. The sense amplifier threshold then decays until the next R-wave is sensed. In this manner the sensing threshold of the sense amplified is continually adjusted to allow for variations in the sensed strength of the R-wave. However, there is still room for improved techniques for eliminating the effects of oversensing.

Accordingly, it is desirable to provide an additional mechanism for dealing with oversensing of depolarization events. In addition, it is desirable to provide an algorithm to be incorporated into detection algorithms in the IMD to prevent the detection and erroneous application of therapies for detected episodes caused by oversensing. Furthermore, other desirable features and characteristics of the present invention will become apparent from the subsequent detailed description and the appended claims, taken in conjunction with the accompanying drawings and the foregoing technical field and background.

BRIEF SUMMARY OF THE INVENTION

A method and apparatus delivering therapy in an implantable medical device that includes sensing a first cardiac signal and detecting cardiac events via a first electrode configuration, determining the presence of an episode requiring therapy in response to the detected cardiac events, sensing a second cardiac signal via a second electrode configuration, comparing, in response to an episode being present, portions of the second cardiac signal corresponding to the detected cardiac events with a predetermined template, and determining whether to deliver therapy in response to the comparing.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
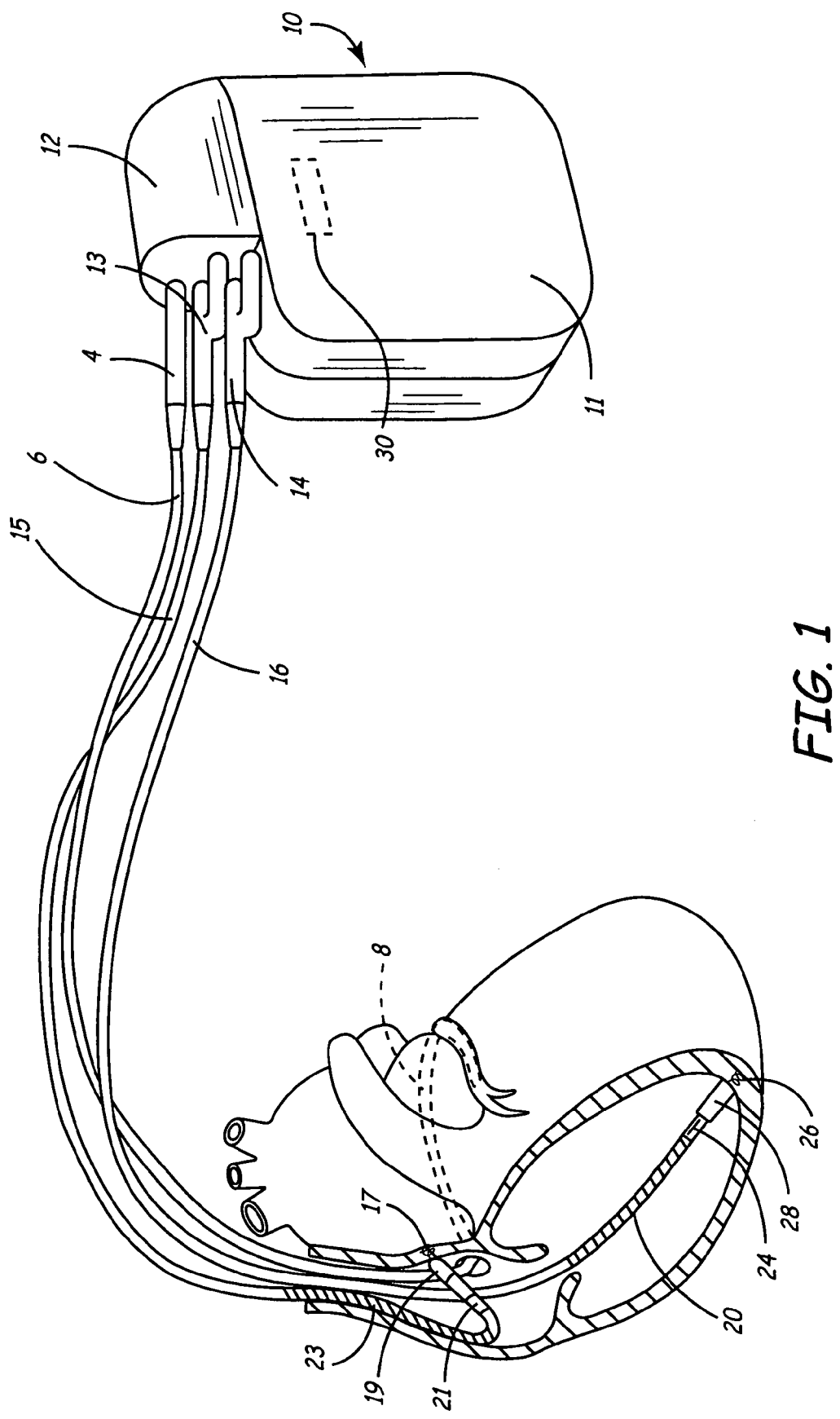
FIG. 1 is a schematic diagram of a pacemaker/cardioverter/defibrillator and lead set of a type in which the present invention may usefully be practiced.

FIG. 1 is a schematic diagram of a pacemaker/cardioverter/defibrillator and lead set of a type in which the present invention may usefully be practiced. The ventricular lead includes an elongated insulative lead body 16, carrying three mutually insulated conductors. Located adjacent the distal end of the lead are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector 14, which carries three electrical connectors, each coupled to one of the coiled conductors.

The atrial/SVC lead includes an elongated insulative lead body 15, also carrying three mutually insulated conductors. Located adjacent the J-shaped distal end of the lead are a ring electrode 21 and an extendible helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13, which carries three electrical connectors, each coupled to one of the coiled conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4 that carries an electrical connector, coupled to the coiled conductor.

The pacemaker/cardioverter/defibrillator 10 includes a hermetic enclosure or housing 11 containing the electronic circuitry used for generating cardiac pacing pulses for delivering cardioversion and defibrillation shocks and for monitoring the patient's heart rhythm. Pacemaker/cardioverter/defibrillator 10 is shown with the lead connector assemblies 4, 13 and 14 inserted into the connector block 12, which serves as a receptacle and electrical connector for receiving the connectors 4, 13 and 14 and interconnecting the leads to the circuitry within housing 11. An optional sensor 30 is illustrated schematically by broken outline, and may include one or more of an activity sensor, respiration sensor (potentially from impedance), accelerometer-based posture detector, heart rate detector, ischemia detector and other available physiological sensor known in the art for measuring heart hemodynamics and may be a piezoelectric transducer as known in the art. Sensor 30 may be used, for example, to regulate the underlying pacing rate of the device in rate responsive pacing modes.

Optionally, insulation of the outward facing portion of the housing 11 of the pacemaker/cardioverter/defibrillator 10 may be provided or the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two lead system.

Figure 2:
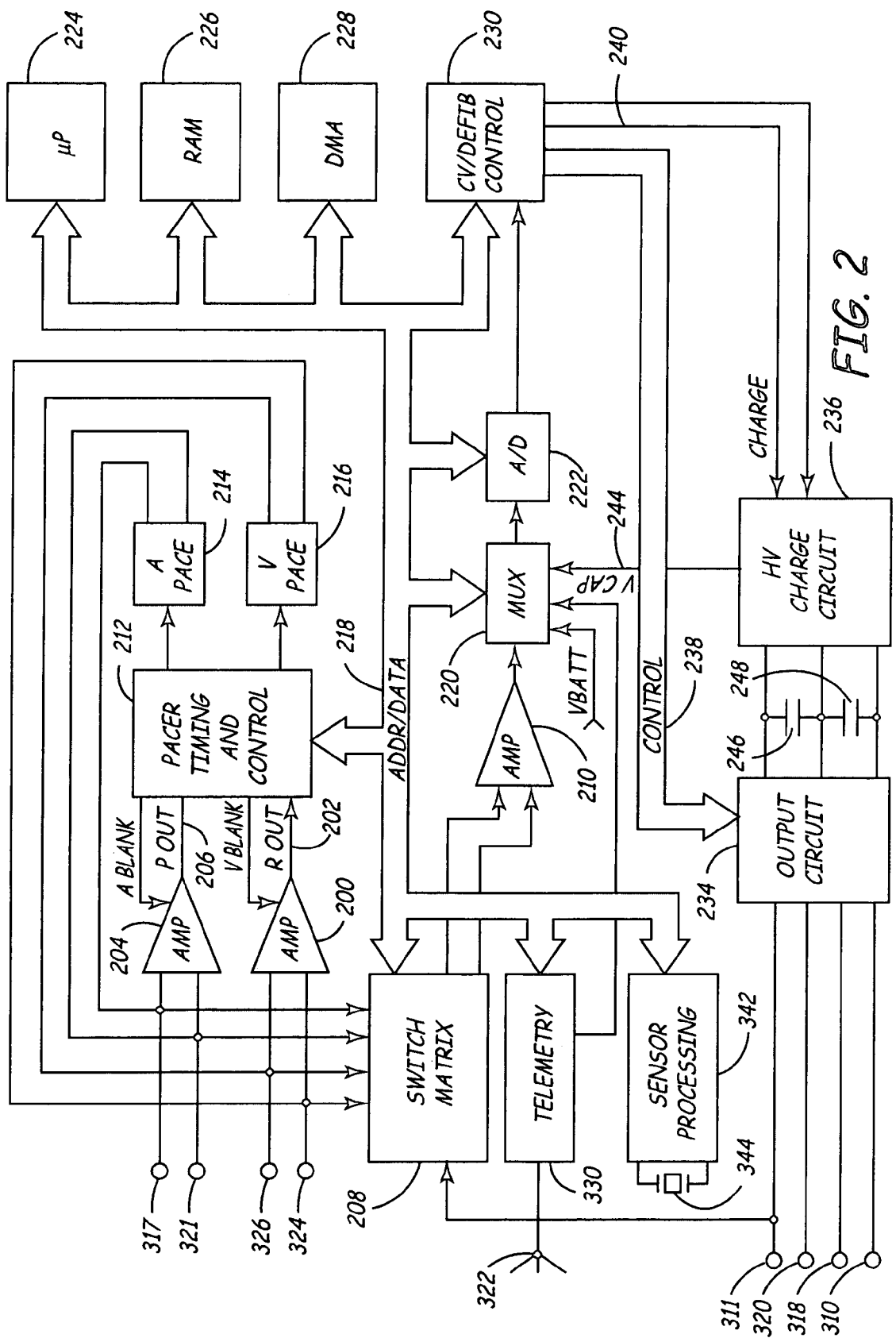
FIG. 2 is a functional schematic diagram of an implantable pacemaker/cardioverter/defibrillator of the type illustrated in FIG. 1, in which the present invention may usefully be practiced.

FIG. 2 is a functional schematic diagram of an implantable pacemaker/cardioverter/defibrillator of the type illustrated in FIG. 1, in which the present invention may usefully be practiced. This diagram should be taken as exemplary of one type of anti-tachyarrhythmia device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to an electrode formed along the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A v-sense signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present invention.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits 200, 204 produce atrial and ventricular EGM signals which also may be digitized and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The device of FIG. 2 includes an optional activity sensor 344, mounted to the interior surface of the device housing or to the hybrid circuit within the device housing and corresponds to sensor 30 of FIG. 1. The sensor 344 and sensor present in circuitry 342 may be employed in the conventional fashion described in U.S. Pat. No. 4,428,378 issued to Anderson et al, incorporated herein by reference in its entirety, to regulate the underlying pacing rate of the device in rate responsive pacing modes.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and are used in conjunction with the present invention to determine oversensing and in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include any of the numerous available prior art tachyarrhythmia detection algorithms. One preferred embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various arrhythmia detection methodologies known to the art might also usefully be employed in alternative embodiments of the invention.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 3:
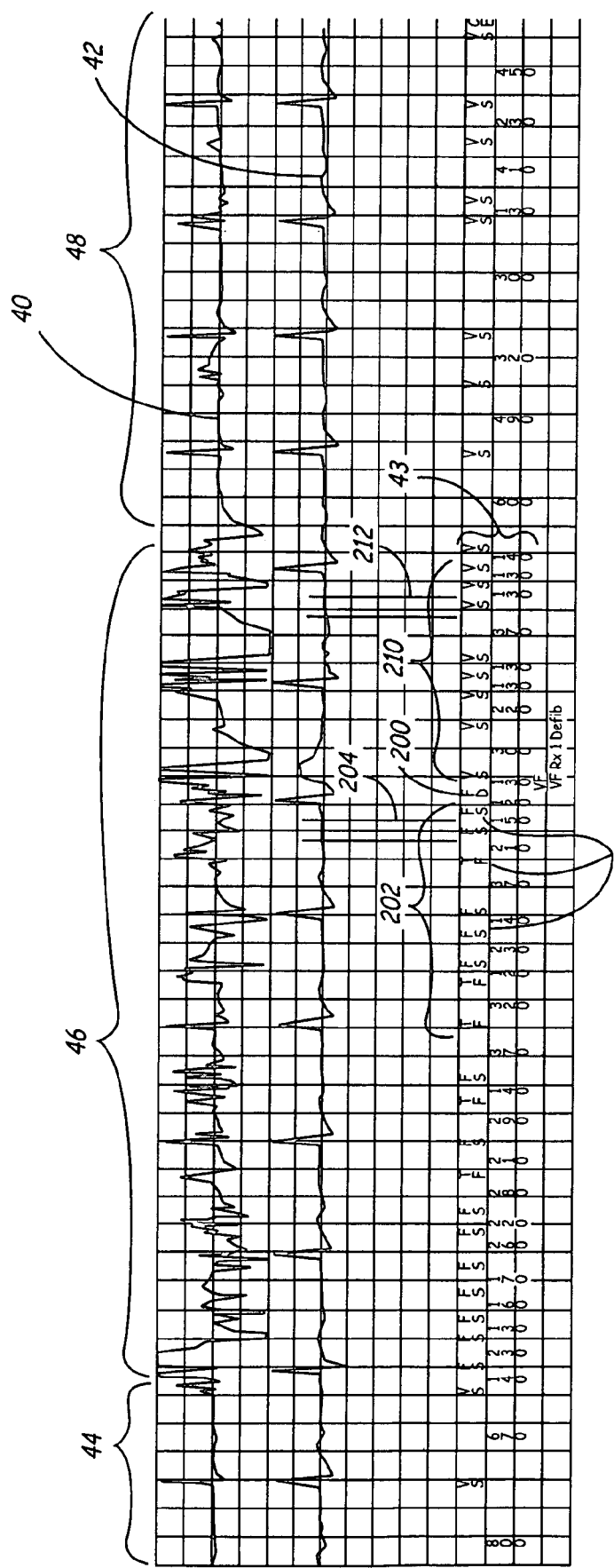
FIG. 3 is a portion of an electrogram showing near-field and far-field R-wave sensing pulses where there is an indication of a false positive near-field pulse.

FIG. 3 is a portion of a stored electrogram showing near-field and far-field pulses where there is an indication of a false positive near-field pulse. As illustrated in FIG. 3, the near-field signal 40 is recorded between the tip and ring electrodes of the bipolar sensing lead, such as electrodes 24 and 26, for example. This signal is input to a sense amplifier that senses voltages that exceed a threshold. The far-field signal 42 is recorded between secondary electrodes such as the lead coil and the can or a sensing lead in another part of the heart (left auricle or right ventricle). A marker channel 43 below far-field electrogram 42 displays each sensed event from the near-field signal, such as Fibrillation Sense (FS), Fibrillation Detected (FD), Tachycardia Sensed (TS) Ventricular Sense (VS) Capacitors charged (CE), or Capacitor Discharged (CD) for example. The numbers below the letters on marker channel 43 indicate the time between sensed events. For example on the left side of FIG. 3 there are two VS events, and the number below and between them is "670", indicating that there were 670 milliseconds between the two VS events. Note that at the left of the electrogram wave 40 is a relatively normal R-wave representation 44. The period of relative normal R-wave representation 44 is followed by a series of erratic signals 46 that indicate an oversensing problem (i.e., a fractured lead conductor or insulation break on the lead).

An examination of far-field signal 42, however, shows a relatively regular far-field R-wave. During the period of relative normal R-wave representation 44, the far-field signal 42 follows the near-field signal 40 quite closely. When the near-field signal 40 becomes erratic in an erratic portion 46, the far-field signal 42 continues to show regular R-wave far-field pulses indicating that the erratic portion 46 may be due to oversensing. As the near-field signal 40 recovers at a period of relative normal R-wave representation 48, the far-field signal 42 continues to follow the near-field signal 40, suggesting that the irregular portion 46 of the near-field signal 40 was due to oversensing, and probably an intermittent failure, since the R-wave pulses of near-field signal 40 recovered at period of relative normal R-wave representation 48.

With a pattern of this nature, it would be premature to deliver a therapy to the patient, particularly a painful defibrillation shock. Typically several methods are used to avoid delivering a shock under these conditions. First, if there is a detection of an irregularity as seen in the erratic portion 46 of near-field signal 40, one can wait to see whether the problem goes away by increasing the number of intervals for detection (as is the case in the waves of FIG. 3), which would suggest that the problem may be an oversensing problem and not an arrhythmia. Also, the sensing lead electrode configuration could be changed, and pacemakers may be programmed to automatically change the sensing lead configuration (e.g. bipolar to unipolar). Finally, the patient could be given an alert (a vibration or audio alert, for example) to advise the patient to see his doctor to have the ICD and its leads checked, but an alert would not prevent the shock at the moment of oversensing.

Figure 4:
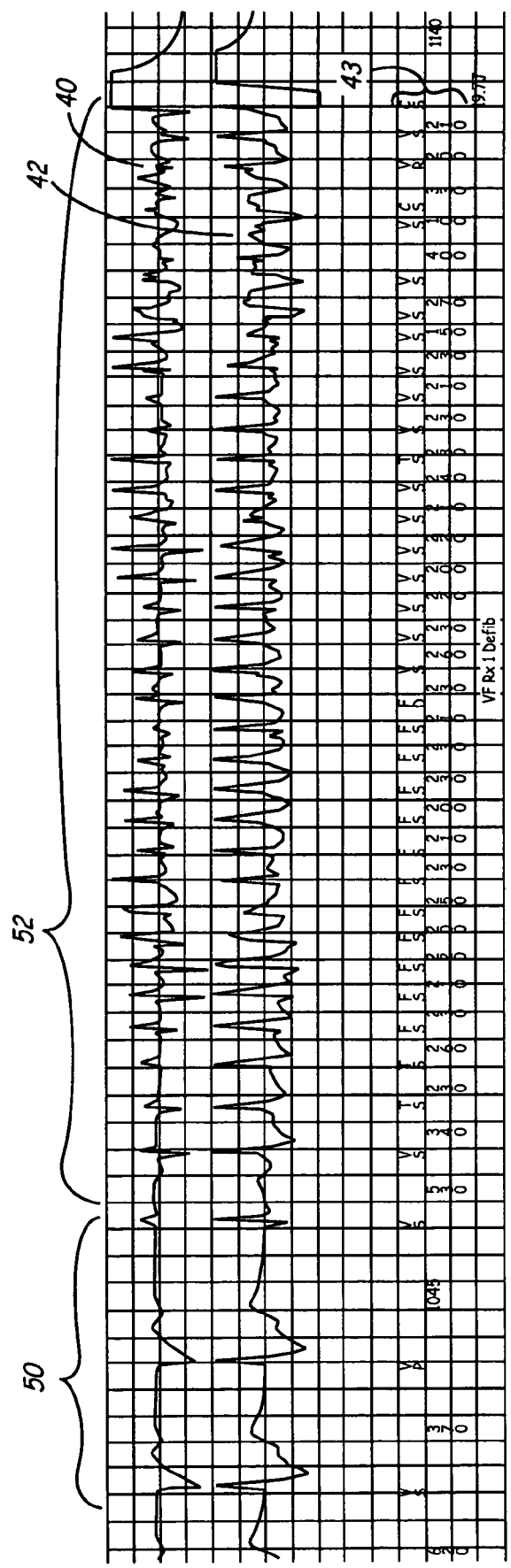
FIG. 4 is a portion of an electrogram showing near-field and far-field R-wave sensing pulses where there is an actual cardiac episode requiring therapy.

FIG. 4 is a portion of an electrogram showing near-field and far-field R-wave sensing pulses where there is an actual cardiac episode requiring therapy. The near-field signal 40 and the far-field signal 42 are shown as in FIG. 3. In this case the beginning (left side) of near-field signal 40 shows relatively normal R-waves in portion 50 (although the pulses are inverted from those of FIG. 3. Likewise far-field signal 42 confirms the regularity during portion 50. At portion 52 of the near-field signal 40, however, a highly irregular waveform exists. Unlike in FIG. 3, however, the far-field wave 42 does not maintain a regular R-wave periodicity during portion 50, but rather confirms the irregularity of near-field signal 40. This would strongly suggest an arrhythmia in the patient's ventricle and call for therapy in the form of a defibrillation shock. As above, however, certain intermediate steps may be taken before actually administering the shock such as waiting a short period of time (perhaps ten or fifteen seconds) to see whether the situation resolves itself. This period of time occurs because the capacitors are charging. If in fact this waveform identifies an arrhythmia event, a therapy must be administered very quickly.

The decision to administer a therapy has been based primarily upon the near-field R-wave. The present invention uses the far-field electrogram to discriminate QRS complexes between supraventricular (e.g. sinus tachycardia, atrial fibrillation) and ventricular arrhythmias. In this way, the present invention provides an algorithm that takes into account other information to provide a better determination of an actual arrhythmia before subjecting a patient to a painful defibrillation shock. The algorithm uses far-field QRS complexes converted to wavelet coefficients to identify both sinus R-waves and noise components (based on an isoelectric baseline for a far-field electrogram) during oversensing. As each ventricular event is sensed on the near-field electrogram, the QRS complex is checked against a stored template to determine whether there was a sinus beat using a match percentage. The sensed R-waves would have a high percentage match with the sinus template and the sensed noise would have a low percentage match. The far-field electrogram isoelectric baseline is determined by calculating the sum of successive samples in the electrogram window. The use of additional information in analyzing R-wave patterns can be useful in identifying an oversensing condition, which, if present, allows the administration of a therapy shock to be delayed until oversensing is confirmed.

Figure 5:
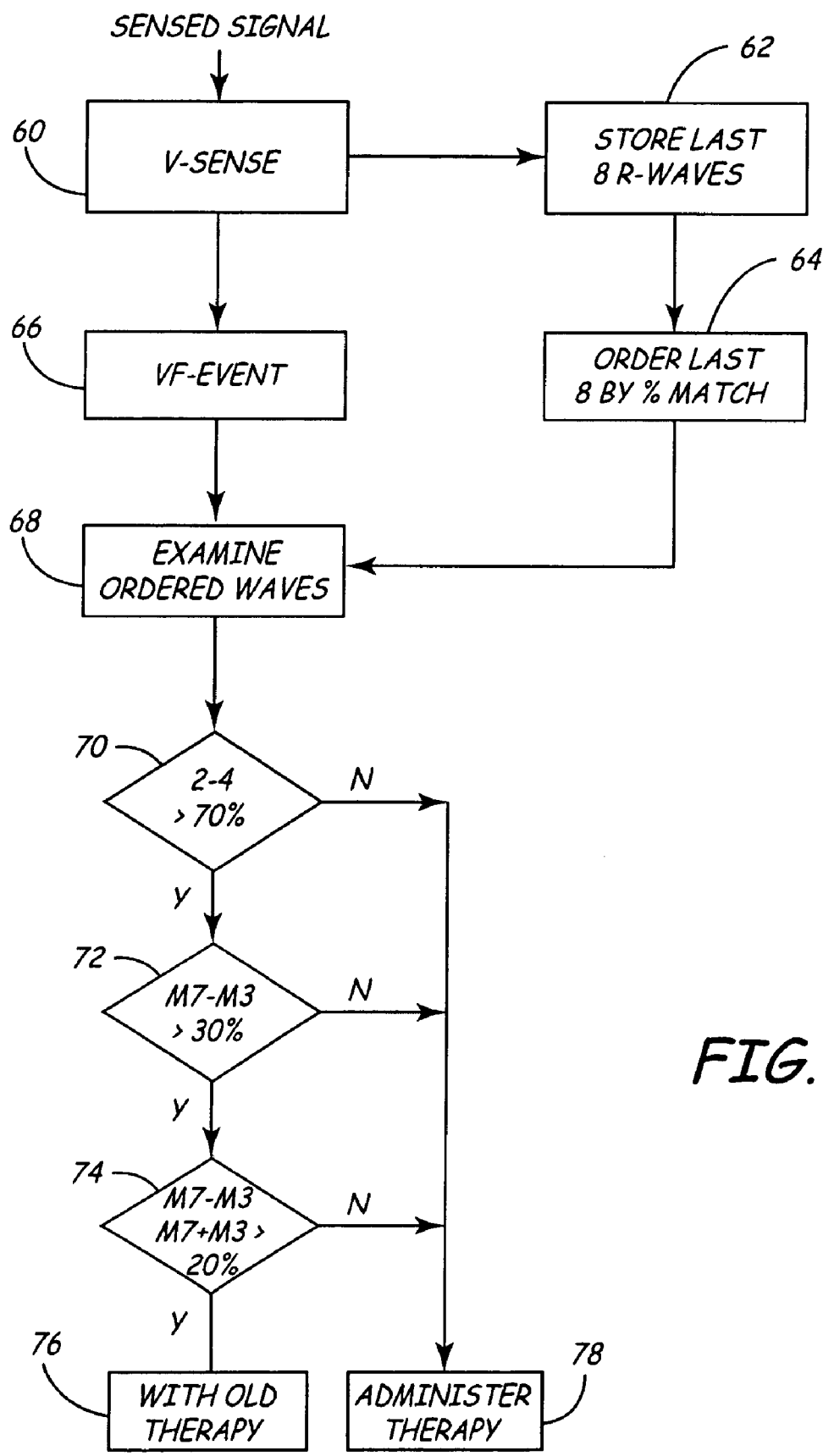
FIG. 5 is a flow diagram of a method of delivering therapy in an implantable medical device, according to an embodiment of the present invention.

FIG. 5 is a flow diagram of a method of delivering therapy in an implantable medical device, according to an embodiment of the present invention. As illustrated in FIGS. 1–2 and 5, each time a V-sense signal is sensed between electrodes 24 and 26, Step 60, the corresponding QRS wave complex is stored in RAM 226 together with the previous seven V-sense signals to form a rolling sequence (i.e., the last eight R-waves received are continuously stored), Step 62. Once a ventricular fibrillation episode is detected using known detection algorithms as described above, Step 66, the last eight R-waves are ordered by percentage match of the R-wave with a predetermined sinus R-wave template, Step 64, to form R-waves M1 through M8, with the eighth ordered R-wave M8 having the largest percentage match and the first ordered R-wave M1 having the lowest percentage match with the template. In this way, upon detection of a ventricular fibrillation episode, the eight most recent ordered R-waves are retrieved from storage and examined, Step 68, and a determination is made as to whether, among the eight sensed events (i.e. order R-waves M1–M8), the percentage match of two to four events is greater than a predetermined percentage, Step 70, such as 70%, for example. This is evidence of the existence of multiple sinus R-waves. While 70% has been chosen as a threshold matching percentage as an example, the actual percentage used may differ as determined by experimentation with particular ICDs, sensors, lead effectiveness, or the like.

If the percentage match of two to four events of the eight ordered events M1–M8 is not 70% or greater, oversensing is not detected, and therefore therapy is delivered in the normal fashion described above, i.e., therapy is not inhibited because of determined oversensing, Step 78. On the other hand, if the percentage match of two to four events of the eight ordered events M1–M8 are 70% or greater, a determination is made as to whether the difference between the template match percentages of the seventh ordered R-wave M7 and the third ordered R-wave M3, i.e., the interquartile percentage range M7–M3, is greater than a selected threshold, Step 72, such as 30%, for example. Again this threshold is somewhat arbitrary and may be subject to modification as set forth above with respect to the determination at Step 70.

If the interquartile range is not greater than the selected threshold, oversensing is not detected, and therefore therapy is delivered in the normal fashion described above, i.e., therapy is not inhibited because of determined oversensing, Step 78. On the other hand, if the interquartile range is greater than the selected threshold, a determination is made as to whether an interquartile variability, i.e., the difference between the match percentages of the seventh ordered R-wave M7 and the third ordered R-wave M3 (M7–M3) divided by the sum of the seventh ordered R-wave M7 and the third ordered R-wave M3 (M7+M3), is greater than a predetermined threshold, Step 74, such as 20%, for example. As with the other thresholds, this threshold is subject to modification in a particular device for the same reasons given above. If the interquartile variability is not greater than the predetermined threshold, oversensing is not detected, and therefore therapy is delivered in the normal fashion described above, i.e., therapy is not inhibited because of determined oversensing, Step 78. On the other hand, if interquartile variability is greater than the predetermined threshold, oversensing is detected, and therapy is withheld, Step 76. The two determinations of Steps 72 and 74 taken together, if successfully passed, offer evidence of a bimodal distribution of matches. If there is in fact a bimodal distribution this is evidence of oversensing, since some true sinus R-waves were detected at Step 70, and there are, by virtue of the determinations at Steps 72 and 74, some non-sinus R-waves.

As an example of the operation of the method illustrated in FIG. 5, assume the following values corresponding to the percentage match of the eight most recently sensed events with the template wave:

M8=87%
M7=85%
M6=61%
M5=40%
M4=31%
M3=28%
M2=19%
M1=13%

Clearly the percentage match of two to four of the eight ordered sensed events is met, Step 70, since two of the percentages, M7 and M8, are above 70%. The interquartile range criterion is also met, Step 72, since the difference between the seventh ordered R-wave and the third ordered R-wave, M7–M3 (85–28=57) is greater than 30%, and the interquartile variability criterion is met, Step 74, since the difference between the match percentages of the seventh ordered R-wave and the third ordered R-wave divided by the sum of the seventh ordered R-wave and the third ordered R-wave (M7–M3)/(M7+M3) (57/113=50.4%) is greater than 20%. Thus in this instance therapy would be withheld because of strong evidence of oversensing.

Likewise, consider the following values for corresponding to the percentage match of the eight most recently sensed events with the template wave:

M8=29
M7=27
M6=25
M5=19
M4=17
M3=15
M2=13
M1=11

With this set of percentages obviously none of the criteria of Steps 70, 72 and 74 are met, and therefore oversensing would not be detected and therefore therapy would not be withheld.

Figure 6:
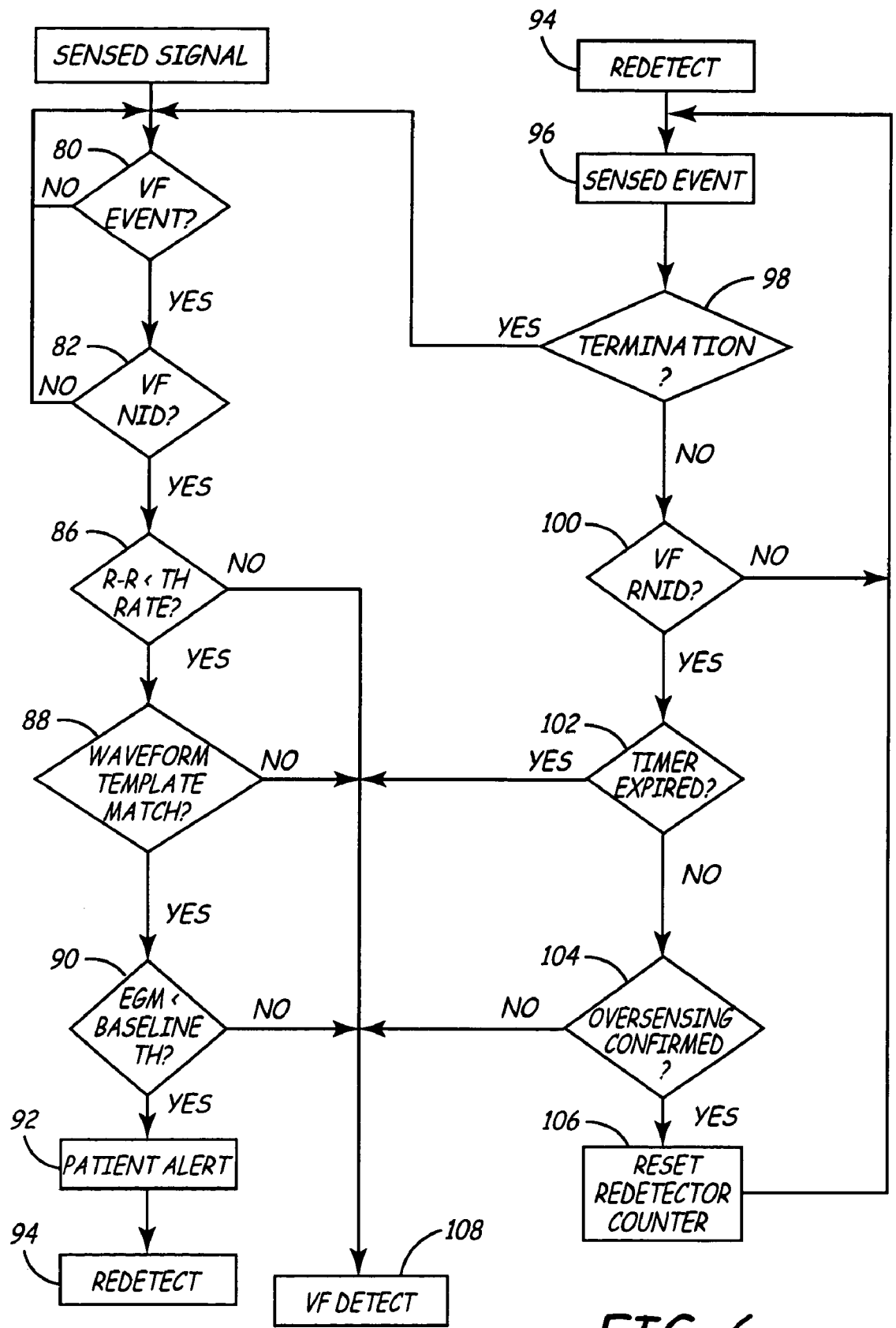
FIG. 6 is a flow diagram of a method of delivering therapy in an implantable medical device, according to an alternate embodiment of the present invention.

FIG. 6 is a flow diagram of a method of delivering therapy in an implantable medical device, according to an alternate embodiment of the present invention. As illustrated in FIGS. 1, 2 and 6, each time a V-sense signal is sensed between a near-field sensor, i.e., electrodes 24 and 26, a determination is made as to whether the sensed event is a VF event, Step 80, with a counter corresponding to the number of sensed events and number of VF events being incremented. In order to ensure that a VF episode is actually taking place, for each VF event sensed, a determination is made as to whether a predetermined number of VF events, i.e., a number of intervals for detection (NID) of ventricular fibrillation (VF), have occurred. For example, a VF episode is determined to be taking place when it is determined that N out of the last M sensed events correspond to VF events, such as 18 out of the last 24 sensed events, or 12 out of the last 18 sensed events correspond to VF events, for example, Step 82. According to the present invention, any desired NIDs can be used.

Once a VF episode is verified, R-R intervals corresponding to the previous M sensed events are evaluated (The numbers under the marker channel 23 in FIGS. 3 and 4 represent the RR intervals) and a determination is made as to whether the R-R intervals are less than a predetermined threshold rate that would indicate the possibility of oversensing, Step 86. For example, according to the present invention, a determination is made in Step 86 as to whether any of the R-R intervals corresponding to the last twelve sensed events are less than a predetermined threshold rate of 160 ms, although it is understood that any number of the last sensed events may be used and that the predetermined threshold rate could include any value desired for indicating the possibility for oversensing.

If none of the evaluated R-R intervals is less than the predetermined threshold, the VF detection process for delivering a corresponding shock therapy continues according to the normal VF detection process, Step 108. However, if there is a possibility of oversensing, i.e., the sensed events include one or more R-R intervals that are less than the predetermined threshold rate, a determination is made as to whether a far-field signal sensed between secondary electrodes within a window of time corresponding to the last eight sensed events matches a predetermined waveform template corresponding to sensing of a sinus beat within a predetermined match threshold, Step 88. As described above, the secondary electrodes for sensing the far-field signal include the lead coil 20 and the uninsulated portion of the housing 11, for example, or a sensing lead 6, 15 in another part of the heart alone or in combination with the uninsulated portion of the housing 11.

In particular, referring back to FIG. 3, given that the VF episode is verified (Yes in Step 82) at sensed event 200, a window 204 corresponding to a predetermined time period prior to and immediately following the eight previous sensed events 202 is evaluated to determine whether the match between the far-field signal corresponding to the windows and the waveform template is greater than the predetermined threshold. According to the present invention, any desired values may be utilized for the window of time and the match threshold. For example, assuming the window of time is set as 200 ms and the match threshold is set as 70%, a portion of the far-field signal 42 corresponding to a 200 ms time window 204 about each of the sensed events 206 is compared to the waveform template to determine whether the match between one of the previous sensed events 206 and the waveform template is within the threshold or better, i.e., the determined match is at 70% or greater. According to the present invention, the waveform match determination of Step 88 can be performed utilizing any of the known waveform matching techniques. An example of such a waveform matching process is described, for example, in U.S. Pat. No. 6,393,316, issued to Gillberg et al., incorporated herein by reference in its entirety.

If none of the waveforms of the far-field sensed events are determined to correspond to a sinus beat, i.e., none of the last eight sensed far-field events matches the predetermined waveform template within the predetermined match threshold, the VF detection process for delivering a corresponding shock therapy continues according to the normal VF detection process, Step 108. However, if it is determined that one or more of the last eight sensed far-field events matches the waveform template within the match threshold, a determination is made as to whether the corresponding far-field signal sensed between the secondary electrodes is below a predetermined baseline threshold indicative of an isoelectric baseline, Step 90. In particular, a determination is made as to whether the summation of the portion of the far-field signal within each window 204 corresponding to the previous eight sensed events 202 is less than a predetermined baseline threshold, such as 3 ms. It is understood that any value may be chosen for the baseline threshold, and therefore the present invention is not intended to be limited to the use of a 3 ms baseline threshold. In this way, identification of an isoelectric baseline in the far-field signal is utilized a third factor in verifying that oversensing is taking place. In addition, methods other than summing the EGM samples may also be utilized to determine a stable far-field signal. For example, a sum of successive differences between events could be used to indicate no change when the sum of successive differences is determined to be less than a predetermined difference threshold.

If it is determined that the far-field signal within the window about each of the sensed events 206 is not below the baseline threshold, the VF detection process for delivering a corresponding shock therapy continues according to the normal VF detection process, Step 108. On the other hand, if the far-field signal within the window about one or more of the previous sensed events is determined to be less than the baseline threshold, a patient alert is activated to alert the patient to have the implanted device checked by their physician. The patient alert may include an audio tone, vibration or other alert. Since at this point all three tests at Steps 86, 88, and 90 have been affirmative, the detected VF episode was most likely caused by oversensing, and therefore the capacitor charging and therapy to the patient is delayed and the IMD goes into a redetect mode to verify the existence of oversensing, Step 94.

During the redetect mode, Step 94, a determination is made as to whether the detected episode has self terminated, Step 98, by evaluating R-R intervals corresponding to sensed V-events occurring subsequent to the detected episode, Step 96, and determining whether a predetermined number of sinus beats, such as eight consecutive sinus beats, for example, are sensed subsequent to the detected episode. Again, self-termination may be determined in response to any number of sensed sinus beats, and therefore it is understood that the present invention is not intended to be limited to the use of eight sinus beats to indicate self-termination of the VF episode. If the detected episode has terminated, Yes in Step 98, the counters are reset and the process waits for the next detected episode, Step 80. If the detected episode has not terminated, a determination is made as to whether a predetermined number of VF events, i.e., a redetection number of intervals for detection (RNID) of ventricular fibrillation (VF), have occurred in order to verify the detected episode, Step 100. For example, a VF episode is determined to be taking place during redetection when it is determined that N out of the last M subsequently sensed events correspond to VF events, such as 6 out 8 subsequently sensed events correspond to VF events. However, it is understood that, according to the present invention, any desired values may be utilized for the RNID.

If the predetermined number of VF events have not occurred, No in Step 100, the process is repeated upon receipt of the next subsequent sensed event, Step 96. Once the detected episode is verified in Step 100, i.e., 6 out of 8 subsequently sensed events correspond to a VF event, a determination is made as to whether a redetection timer has expired, Step 102. If the redetection timer has expired and the redetection of oversensing has not been confirmed, the VF detection process for delivering a corresponding shock therapy continues according to the normal VF detection process, Step 108. If the redetection timer has not expired, a determination is made as to whether oversensing is confirmed by the subsequently sensed events 210 (FIG. 3), Step 104. In particular, as illustrated in FIGS. 3 and 6, oversensing is confirmed in Step 104 by determining, similar to Step 86, whether R-R intervals corresponding to M sensed events 210 subsequent to sensed event 200 are less than the predetermined threshold rate indicative of the possibility of oversensing, whether the far-field signal sensed between secondary electrodes within a window of time 212 corresponding to the subsequent eight sensed events 210 matches the predetermined waveform template, similar to Step 88, and whether the far-field signal corresponding to the subsequent eight sensed events 210 is below the baseline threshold indicative of the EGM having an isoelectric baseline within that window, similar to Step 90.

If oversensing is not confirmed, the VF detection process for delivering a corresponding shock therapy continues according to the normal VF detection process, Step 108. If oversensing is confirmed, the redetect counters are reset, Step 106, and the process is repeated with the next sensed event, Step 96. In this way, the present invention continues to withhold the delivery of therapy because of oversensing unless the oversensing cannot be confirmed, NO in Step 104, the detected episode terminates itself, YES in Step 98, or the timer has expired before the detected episode self terminates or the oversensing fails to be confirmed, Step 102. The redetect timer is a timer that may be set by a doctor depending on the condition of the patient, and represents the time the doctor is willing to allow to delay therapy for a true ventricular arrhythmia. According to an embodiment of the present invention, the timer is set at 5 seconds, although it is understood that any value can be chosen as desired.

Figure 7:
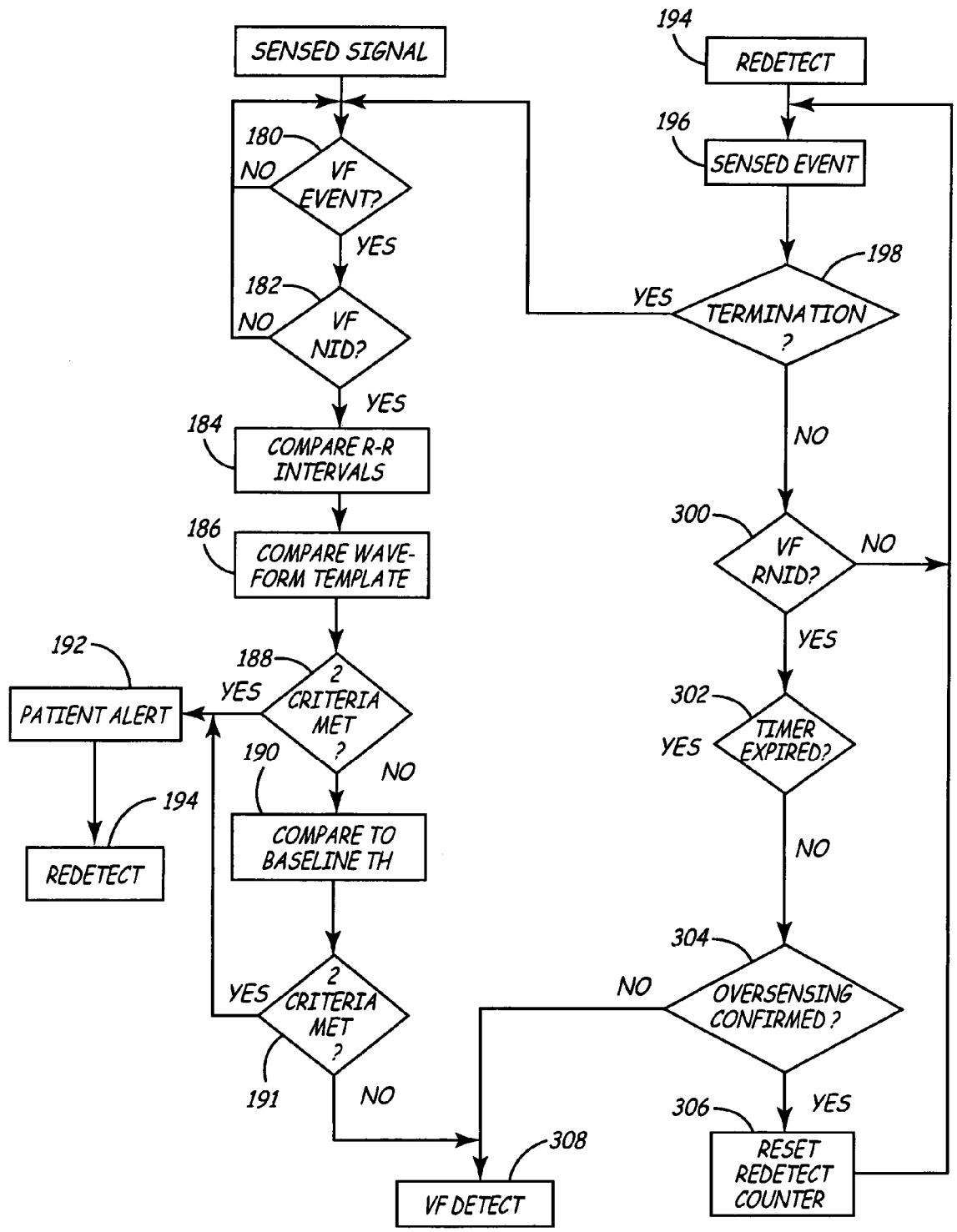
FIG. 7 is a flow diagram of a method of delivering therapy in an implantable medical device, according to an alternate embodiment of the present invention.

FIG. 7 is a flow diagram of a method of delivering therapy in an implantable medical device, according to an alternate embodiment of the present invention. The method of delivering therapy illustrated in FIG. 7 differs from the method described above in reference to FIG. 6 only in that the process for determining whether oversensing is likely occurring, Steps 86, 88 and 90 are replaced in FIG. 7 by Steps 184, 186, 188, 190 and 191. In particular, in the method of determining oversensing according to the embodiment illustrated in FIG. 7, once a VF episode is verified, YES in Step 182, the R-R intervals corresponding to the subsequent eight sensed events 210 are compared to the predetermined threshold rate, i.e., 160 ms for example, Step 184, and the far-field signal sensed between the secondary electrodes within a window of time corresponding to the subsequent eight sensed events 210 is compared to the predetermined waveform template corresponding to a sinus beat, Step 186. A determination is then made, Step 188, as to whether two oversensing criteria have been met, i.e., whether both one or more of the R-R intervals are less than the threshold rate and the far-field signal corresponding to the subsequent eight sensed events matches the predetermined waveform template corresponding to a sinus beat within the predetermined match threshold, similar to Steps 86 and 88 of FIG. 6.

If two oversensing criteria have not been met, a the far-field signal sensed between the secondary electrodes corresponding to the subsequent sensed events 210 is compared to the baseline threshold indicative of an isoelectric baseline in the corresponding EGM, Step 190. A determination is then made, Step 191, as to whether two oversensing criteria have been met, i.e., both one or more of the R-R intervals are less than the threshold rate and the far-field signal sensed between the secondary electrodes corresponding to the subsequent sensed events 210 is less than the baseline threshold, similar to satisfying both Steps 86 and 90 in FIG. 6, or both the far-field signal corresponding to the subsequent eight sensed events matches the predetermined waveform template corresponding to a sinus beat within the predetermined match threshold and the far-field signal sensed between the secondary electrodes corresponding to the subsequent sensed events 210 is less than the baseline threshold, similar to satisfy both Steps 88 and 90 in FIG. 6.

In this way, in the method of detecting oversensing illustrated in FIG. 7, oversensing is detected once two of the three oversensing criteria are met, rather than all three having to be met as described in FIG. 6, and if two of the three oversensing criteria are not met, the VF detection process for delivering a corresponding shock therapy continues according to the normal VF detection process, Step 308, rather than once one of the criteria is not met as described in FIG. 6. In the same way, confirmation of oversensing, Step 304, during redetection, Step 194, would include a repeat of Steps 184–191 using subsequent sensed signals, similar to the redetection Step 94 of FIG. 6.

Other embodiments, based on variations in the embodiments describe in FIGS. 6 and 7, are possible. For example, in an other embodiments, all three of the oversensing criteria would need to be satisfied, as in FIG. 6, for the initial detection of oversensing, Steps 86–90, while only two of three oversensing criteria, Steps 184–191, would need to be satisfied during the redetect portion, i.e., Step 84. In yet another embodiment, only two of three oversensing criteria would need to be satisfied for the initial detection of oversensing, while all three of the oversensing criteria would need to be satisfied during the redetection portion. In addition, although charging of capacitors 246 and 248 by HV charge circuit 236 would be initiated as part of Step 88, 188 so that the battery life of the device would be increased, it is contemplated that the charging of capacitors 246 and 248 could occur simultaneous with or at any time subsequent to the patient alert, Step 92, 192 so that the time to shock is reduced in the event that the oversensing is not confirmed during the redetect.

It should be noted that upon the occurrence of a therapy shock being administered, a number of the R-waves (both near-field and far-field) both prior to and subsequent to the shock are stored within the ICD for later read-out and analysis by a doctor. Depending upon the amount of storage memory within the ICD, the duration of stored waves prior to and after the therapy, and the number of waves stored (i.e. near-field, far-field, others) a number of events can be stored over a period of days or longer. If, for example there is stored only the near-field R-wave, twenty or more minutes of storage would allow forty separate events to be stored. If near-field and far-field R-waves were stored, perhaps only ten minutes would be available for storage. Because of the ability to store several traces of R-waves or other waves of an electrogram, the read-out could also be used in a remote monitoring system in which a patient may connect, for example, a home monitor that downloads the information for later transmission by modem or other convenient means to a doctor's office.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A method for delivering therapy in an implantable medical device, comprising:

sensing a first cardiac signal and detecting cardiac events via a first electrode configuration;

determining the presence of an episode requiring therapy in response to the detected cardiac events;

determining a possibility of oversensing by evaluating an R-R interval of each of a predetermined number of the detected cardiac events, associated with the episode, by comparing each R-R interval to a predetermined time threshold, sensing a second cardiac signal via a second electrode configuration;

comparing portions of the second cardiac signal, which are each aligned with a corresponding time window surrounding each of the predetermined number of the detected cardiac events, with a predetermined template, if any of the R-R intervals are less than the predetermined time threshold; and determining whether to deliver therapy in response to the comparing.

2. The method of claim 1, wherein the comparing further comprises:

determining whether any of the portions of the second cardiac signal matches the predetermined template.

3. The method of claim 2, further comprising summing the portions of the second cardiac signal, if at least one of the portions matches the predetermined template within a match threshold; and wherein determining whether to deliver therapy is further in response to the summation of the portions.

4. The method of claim 3, wherein determining whether to deliver therapy comprises inhibiting therapy delivery in response to a determination that the second cardiac signal, corresponding to the portions, has an isoelectric baseline based upon the summation of the portions.

5. The method of claim 4, further comprising activating a patient alert.

6. The method of claim 1, wherein the first cardiac signal is a near-field signal and the second cardiac signal is a far-field signal.

* * * * *

UNITED STATES PATENT AND TRADEMARK OFFICE
CERTIFICATE OF CORRECTION

PATENT NO. : 7,167,747 B2
APPLICATION NO. : 10/436626
DATED : January 23, 2007
INVENTOR(S) : Gunderson et al.

It is certified that error appears in the above-identified patent and that said Letters Patent is hereby corrected as shown below:

Title page, inventors item (75) to read as follows: "Bruce D. Gunderson, Plymouth, MN (US); Jeffrey M. Gillberg, Coon Rapids, MN (US); Jay M. Wilcox, St. Paul, MN (US)"

Signed and Sealed this

Twentieth Day of July, 2010

David J. Kappos
*Director of the United States Patent and Trademark Office*